(12) United States Patent
Rezachek

(10) Patent No.: US 8,746,038 B2
(45) Date of Patent: Jun. 10, 2014

(54) PHOTOACOUSTIC DETECTOR WITH ACOUSTIC AND VIBRATION NOISE COMPENSATION

(75) Inventor: Tom M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 399 days.

(21) Appl. No.: 13/078,032

(22) Filed: Apr. 1, 2011

(65) Prior Publication Data

US 2012/0247183 A1 Oct. 4, 2012

(51) Int. Cl.
*G01N 21/17* (2006.01)
(52) U.S. Cl.
USPC .......................... 73/24.02; 356/932
(58) Field of Classification Search
CPC .................. G10N 21/1702; G01N 2021/1704; G01N 2021/1708; G01N 29/2418; G01N 29/2425
USPC ........................... 73/24.02; 356/932
See application file for complete search history.

(56) References Cited

U.S. PATENT DOCUMENTS

| | | | | |
|---|---|---|---|---|
| 4,594,004 A | * | 6/1986 | Ishida et al. | 356/433 |
| 4,817,413 A | * | 4/1989 | Asano et al. | 73/24.02 |
| 6,006,585 A | * | 12/1999 | Forster | 73/24.01 |
| 6,305,212 B1 | * | 10/2001 | Drzewiecki | 73/23.2 |
| 7,034,943 B1 | * | 4/2006 | Moeckli et al. | 356/423 |
| 7,069,769 B2 | * | 7/2006 | Kung | 73/24.02 |
| 7,091,869 B2 | * | 8/2006 | Forster et al. | 340/628 |
| 7,213,444 B2 | * | 5/2007 | Baraket et al. | 73/24.01 |
| 7,244,939 B2 | | 7/2007 | Stuttard | 250/343 |
| 2005/0160791 A1 | * | 7/2005 | Kung | 73/24.02 |
| 2006/0192966 A1 | * | 8/2006 | Moeckli et al. | 356/437 |
| 2006/0254340 A1 | * | 11/2006 | Baraket et al. | 73/24.01 |
| 2008/0252891 A1 | * | 10/2008 | Uber | 356/437 |
| 2009/0320561 A1 | | 12/2009 | Fritz et al. | 73/24.02 |
| 2010/0020326 A1 | * | 1/2010 | Van Kesteren | 356/437 |
| 2010/0027012 A1 | | 2/2010 | Fritz et al. | 356/432 |
| 2010/0045998 A1 | | 2/2010 | Fritz et al. | 356/450 |
| 2010/0147051 A1 | | 6/2010 | Tobias | 73/24.02 |
| 2010/0242572 A1 | * | 9/2010 | Yu | 73/24.02 |

* cited by examiner

*Primary Examiner* — Hezron E Williams
*Assistant Examiner* — Nathaniel Kolb
(74) *Attorney, Agent, or Firm* — Husch Blackwell LLP

(57) ABSTRACT

A photoacoustic detector includes a sensing region for receiving atmospheric samples. One microphone receives acoustic samples from the sensing region. Another microphone receives acoustic samples from a displaced region. Microphone outputs can be subtracted to eliminate common noise and to generate an indicium of gas present in the sensing region.

16 Claims, 3 Drawing Sheets

PHOTOACOUSTIC DETECTOR WITH ACOUSTIC AND VIBRATION NOISE COMPENSATION

FIELD

This application pertains to photoacoustic detectors. More particularly, the application pertains to such detectors which include circuitry to remove acoustic noise.

BACKGROUND

Various types of photoacoustic sensors are known to detect gases. These include, Fritz et al., US Patent Application No. 2009/0320561, published Dec. 31, 2009 and entitled "Photoacoustic Cell"; Fritz et al., US Patent Application No. 2010/0027012, published Feb. 4, 2010 and entitled, "Photoacoustic Spectroscopy System"; and Fritz et al., US Patent Application No. 2010/0045998, published Feb. 25, 2010 and entitled "Photoacoustic Sensor". The above noted published applications have been assigned to the assignee hereof, and are incorporated herein by reference.

Such sensors, while useful, can be affected by acoustic and mechanical vibration noise sources. Such sources can create significant errors when their frequency content contains components at or near the operational frequency of the respective sensor.

DETAILED DESCRIPTION

Figure 1:
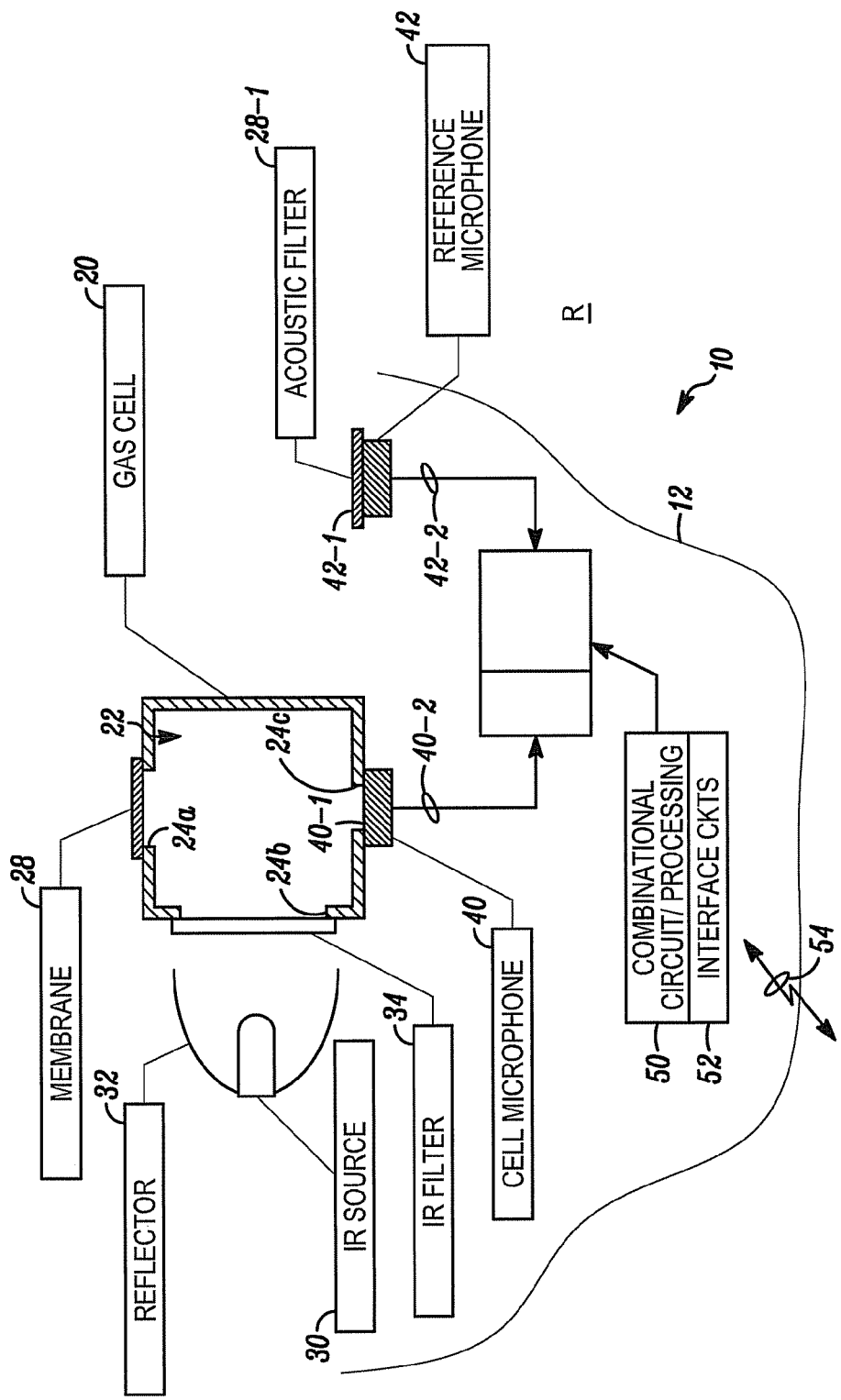
FIG. 1 is a block diagram of a detector in accordance herewith.

While embodiments can take many different forms, specific embodiments thereof are shown in the drawings and will be described herein in detail with the understanding that the present disclosure is to be considered as an exemplification of the principles hereof, as well as the best mode of practicing same. No limitation to the specific embodiment illustrated is intended.

In a disclosed embodiment, noise can be eliminated in a photoacoustic detector by using two microphones. A first microphone is connected to a gas cell. This microphone responds to the photoacoustic signal and any acoustic noise signal. The second microphone is not connected to the gas cell but is exposed to the environment. This microphone responds to just the acoustic noise signal.

The signals from the two microphones can be combined to remove the common acoustic noise. Preferably, the microphones will be mounted with the same orientation relative to a selected plane so that vibration related noise will act equally on both microphone diaphragms.

The cell has an input port which is covered with a diffusion membrane. The second microphone is covered by an acoustic filter which is sealed to the sound port. The acoustic filter is designed to replicate the acoustic behavior of the cell and membrane connected to the first microphone.

FIG. 1 illustrates an embodiment 10 of a photoacoustic detector in accordance herewith. Detector 10 can include a housing 12 suitable for portable or fixed use such as by attachment to a wall, ceiling or other mounting structure as desired. Detector 10 can monitor gas concentration in a region R.

Detector 10 includes a sensing chamber, or gas cell 20. The cell 20 can have a variety of shapes as would be understood by those of skill in the art. The shape of the cell 20 is exemplary only.

Cell 20 defines an internal region indicated generally 22 with an atmospheric/environmental input port 24a. Port 24a is covered by a gas permeable membrane 28.

Cell 20 defines a light, or radiant energy input port 24b which can receive infra-red radiant energy from a source 30. Radiant energy from the source 30 can be focused by a reflector 32 and filtered by a filter 34 carried by the cell 20 adjacent to the port 24b.

Cell 20 also defines an acoustic port 24c to which is coupled a first microphone 40. The microphone 40 has an audio input port 40-1. A second, or reference microphone 42 has an audio input port 42-1 which is covered by an acoustic filter 28-1.

The membrane 28 in combination with the cell 20, and acoustic filter 28-1 have substantially identical acoustic attenuating characteristics relative to respective microphones 40, 42. The microphone 40 responds to audio inputs, including noise, from within the region 22. The reference microphone 42 is oriented and carried on the housing 12 to respond to audio inputs such as noise from the ambient environment in the vicinity of the detector 10. Both microphones can have the same orientation relative to a predetermined plane to equalize the effects of vibratory noise.

Control circuitry 50, which could be combinational, or sequential, or both, receives signals, on lines 40-2 and 42-2, from both microphones 40, 42. As discussed subsequently, the common mode noise can be eliminated by subtracting the two signals.

Control circuitry 50 can be coupled to source 30 so as to modulate same at a selected frequency, as would be understood by those of skill in the art. Also as would be understood by those of skill in the art the control circuitry 50 can include wired or wireless interface circuitry 52 so that the detector 10 can communicate with an associated monitoring system, or diagnostic and test equipment via a wired or wireless medium 54.

Figure 2:
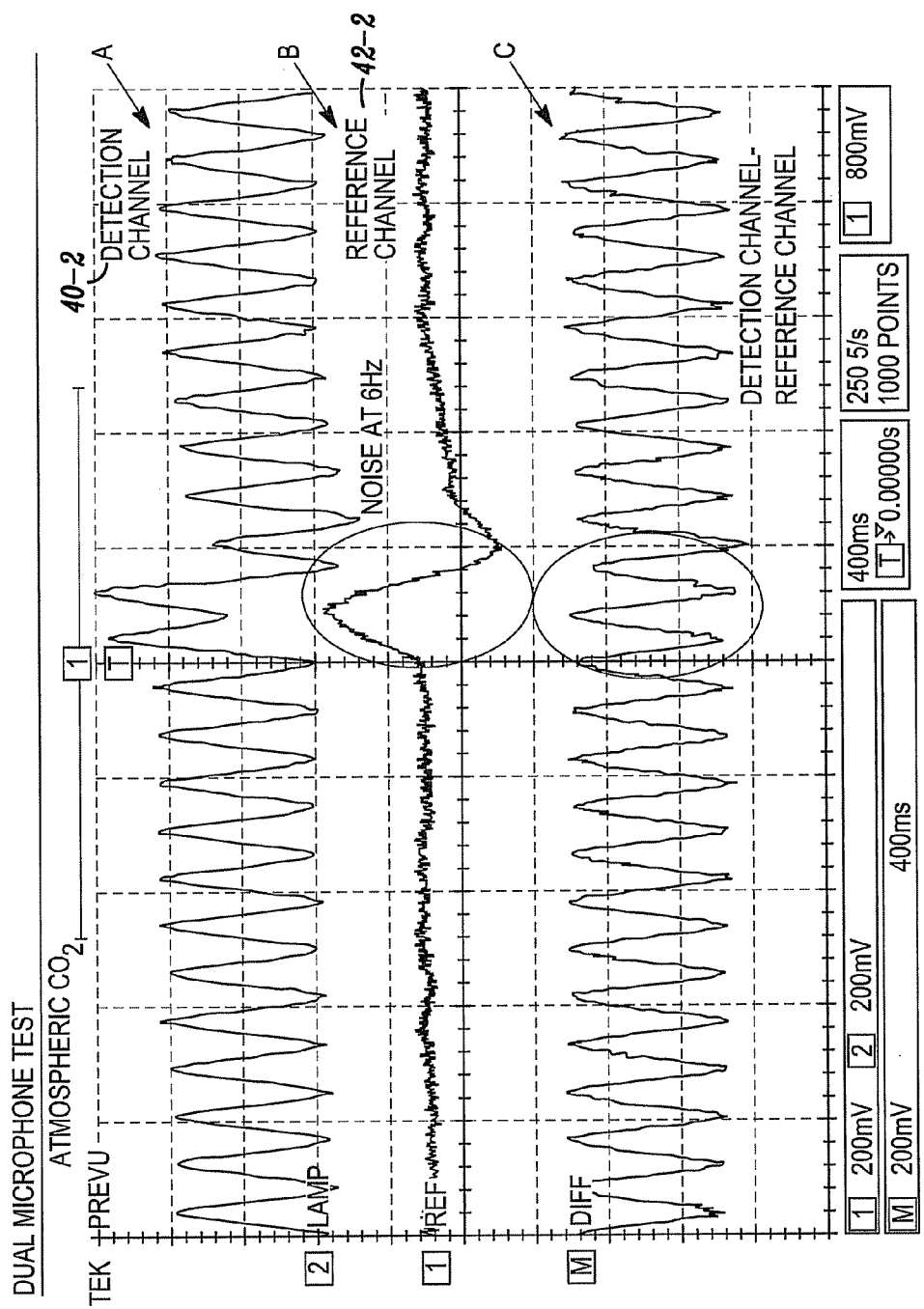
FIG. 2 is a set of graphs which illustrate operational aspects of the detector of FIG. 1.

FIG. 2 illustrates the cell signal A, labeled, detection channel detected by microphone 40, reference signal B detected by microphone 42 and the noise free difference signal C. Signal C could be processed to make a gas concentration determination.

Figure 3A:
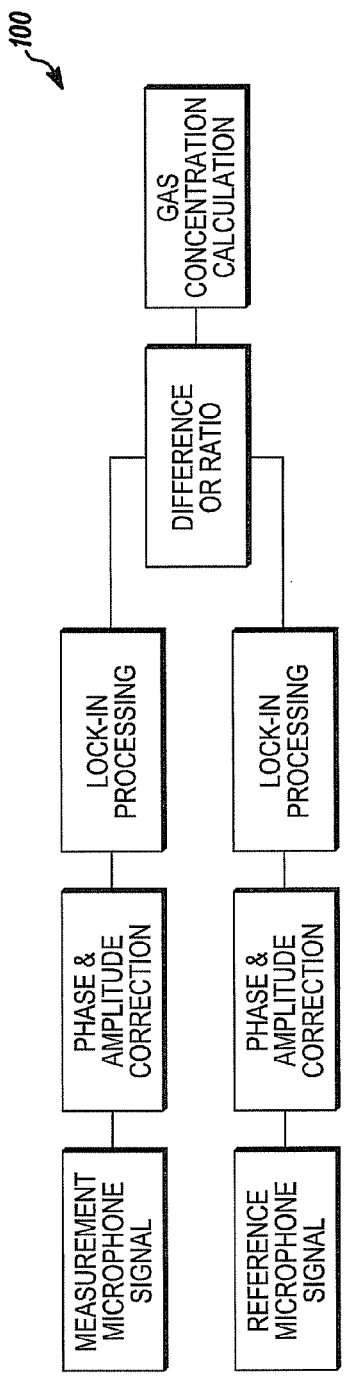
FIGS. 3A, 3B illustrate exemplary signal processing.
Figure 3B:
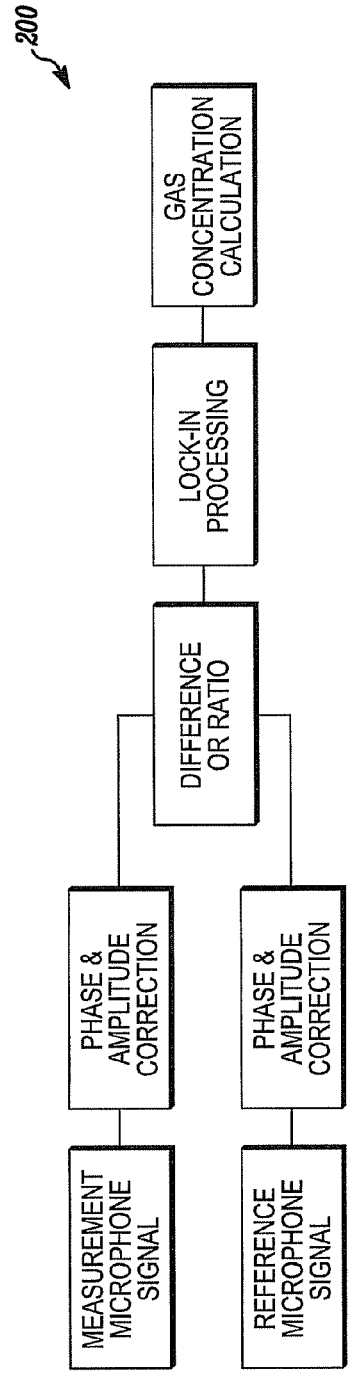

FIGS. 3A, 3B illustrate exemplary processing 100, 200 which can be carried out by the detector 10. Alternately, instead of carrying out the processing locally, the signals from the microphones 40, 42 can be transmitted via interface circuits 52 to displaced circuitry for processing.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacoustic detector for monitoring an ambient region, the detector comprising:
   a sensing chamber having an input port covered by a diffusion membrane;
   a source that directs radiant energy into the chamber; and
   first and second microphones, the second microphone covered by an acoustic filter,
   where the diffusion membrane in combination with the sensing chamber and the acoustic filter have identical acoustic attenuating characteristics relative to the respective first and second microphones, where the first microphone is oriented to detect acoustic activity in the chamber, and where the second microphone is carried on a detector housing and oriented to detect acoustic activity in the ambient region.

2. A detector as in claim 1 which includes control circuits coupled at least to the first and second microphones.

3. A detector as in claim 2 where the control circuits process outputs received from the microphones.

4. A detector as in claim 3 where the control circuits form a difference between the outputs of the microphones.

5. A detector as in claim 4 where the control circuits determine a gas concentration in response to the formed difference.

6. A detector as in claim 3 where the control circuits include at least one of combinational processing circuits, or, sequential processing circuits.

7. A detector as in claim 6 where the sequential processing circuits include a programmed processor, and, pre-stored executable instructions.

8. A detector as in claim 3 where the first microphone is coupled to the sensing chamber.

9. A detector as in claim 3 with a filter positioned between the source and the sensing chamber.

10. A photoacoustic detector for monitoring an ambient region the detector comprising:
    a housing;
    a sensing chamber carried by the housing, the chamber has an input port which is covered by a gas permeable membrane;
    a source of radiant energy;
    an optical filter between the sensing chamber and the source configured to direct radiant energy into the chamber;
    a first microphone carried on the housing and configured to respond to acoustic events in the sensing chamber;
    a second microphone carried on the housing and covered by an acoustic filter, the second microphone is configured to respond to acoustic events in the ambient region; and
    control circuits coupled at least to the microphones, and responsive thereto, the control circuits form a difference signal between outputs of the microphones, where the gas permeable membrane in combination with the sensing chamber and the acoustic filter have identical acoustic attenuating characteristics relative to the respective first and second microphones.

11. A detector as in claim 10 where the control circuits, responsive to the difference signal, determine a gas concentration in the chamber.

12. A detector as in claim 11 where the control circuits, modulate the source of radiant energy.

13. A method comprising:
    providing a first sample of ambient atmosphere within a gas cell having an input port covered by a diffusion membrane;
    directing modulated infra-red radiant energy into the first sample;
    providing a first acoustic output from the first sample indicative of gas therein through a first microphone;
    providing a second sample of ambient atmosphere;
    exposing a second microphone to the ambient atmosphere;
    covering the second microphone by an acoustic filter where the diffusion membrane in combination with the gas cell and the acoustic filter have identical acoustic attenuating characteristics relative to the respective first and second microphones;
    providing a second acoustic output from the second sample through the second microphone;
    combining the acoustic outputs;
    generating a difference signal between the acoustic outputs, the difference signal eliminating common acoustic noise; and
    generating a different signal indicative of a presence of gas in the first sample.

14. A method as in claim 13 which includes filtering the infrared radiant energy prior to directing the infra-red radiant energy into the first sample.

15. A method as in claim 13 which includes enabling the first sample to diffuse into a sampling region through a permeable membrane.

16. A method as in claim 13 which includes filtering an input corresponding to the second acoustic output.

* * * * *